(12) United States Patent
Jethrow et al.

(10) Patent No.: US 6,979,428 B2
(45) Date of Patent: Dec. 27, 2005

(54) FLUID OVER-FLOW/MAKE-UP AIR ASSEMBLY FOR REPROCESSOR

(75) Inventors: Christopher A. Jethrow, Maple Heights, OH (US); Jude A. Kral, Twinsburg, OH (US); Donald A. Sargent, Wickliffe, OH (US)

(73) Assignee: Steris Inc., Temecula, CA (US)

( * ) Notice: Subject to any disclaimer, the term of this patent is extended or adjusted under 35 U.S.C. 154(b) by 71 days.

(21) Appl. No.: 10/633,342

(22) Filed: Aug. 1, 2003

(65) Prior Publication Data

US 2005/0025684 A1 Feb. 3, 2005

(51) Int. Cl.[7] .............................................. A61L 2/00
(52) U.S. Cl. .......................... 422/292; 55/490; 96/226; 96/227; 222/189.06; 222/189.09; 422/122; 422/295
(58) Field of Search ................................ 422/292, 295, 422/297, 110, 112, 113, 122; 222/189, 213, 222/189.06, 189.09; 55/490; 96/226, 227

(56) References Cited

U.S. PATENT DOCUMENTS

| | | | | |
|---|---|---|---|---|
| 4,533,068 A | * | 8/1985 | Meierhoefer | 222/189.09 |
| 4,731,222 A | * | 3/1988 | Kralovic et al. | 422/37 |
| 5,217,698 A | * | 6/1993 | Siegel et al. | 422/295 |
| 5,529,750 A | * | 6/1996 | Kochte | 422/28 |
| 5,591,396 A | * | 1/1997 | Chiffon et al. | 422/26 |
| 5,928,516 A | * | 7/1999 | Hopkins et al. | 210/636 |

* cited by examiner

Primary Examiner—Krisanne Jastrzab
(74) Attorney, Agent, or Firm—Kusner & Jaffe; Michael A. Centanni

(57) ABSTRACT

A system for sterilizing or microbially deactivating instruments and devices. The system includes a circulation system for circulating a microbial deactivation fluid through a chamber for containing the instruments and devices. The chamber forms a portion of the circulation system. The system further includes a fluid over-flow/make-up air assembly. The fluid over-flow/make-up air assembly includes a manifold having an inner cavity that is in fluid communication with the circulation system, an overflow port in the manifold, and an overflow valve assembly disposed in the manifold allowing fluid flow from the cavity to the overflow port when a pressure in the cavity exceeds a pressure in the overflow port by a predetermined amount. A filter assembly is attached to the manifold. The filter assembly has a filter valve assembly in communication with the cavity. The filter assembly is operable to allow air through the filter assembly into the cavity when the pressure within the cavity is a predetermined amount less than the pressure within the filter assembly.

21 Claims, 10 Drawing Sheets

FLUID OVER-FLOW/MAKE-UP AIR ASSEMBLY FOR REPROCESSOR

FIELD OF THE INVENTION

The present invention relates to the microbial deactivation of medical, dental, pharmaceutical, veterinary or mortuary instruments and devices, and more particularly to a fluid over-flow block with makeup-air assembly for use in a microbial deactivation system.

BACKGROUND OF THE INVENTION

Medical, dental, pharmaceutical, veterinary or mortuary instruments and devices that are exposed to blood or other body fluids require thorough cleaning and anti-microbial deactivation or sterilization between each use. Liquid microbial deactivation systems are now widely used to clean and deactivate instruments and devices that cannot withstand the high temperatures of a steam sterilization system. Liquid microbial deactivation systems typically operate by exposing the medical devices and/or instruments to a liquid disinfectant or sterilization composition, such as peracetic acid or some other strong oxidant.

In such systems, the instruments or devices to be cleaned are typically placed within a chamber within the liquid microbial deactivation system, or in a container that is placed within the chamber. A liquid disinfectant is then circulated through a liquid circulation system that includes the chamber (and the container therein) during a sterilization or microbial deactivation cycle.

The circulation system typically includes an air purge/fluid overflow assembly to allow air to be purged from the system during the filling of the circulation system. A "make-up" air system is also provided to allow air to enter the circulation system when the liquid deactivation fluid is drained therefrom.

A problem with such air purge/fluid overflow assembly and air make-up assemblies is preventing biological contaminants from entering the chamber (and container) when external air is drawn into the chamber after a sterilization or deactivation cycle. With respect to the air make-up assembly, it is known to use a HEPA-grade filter to filter the incoming air, but the filtering of the incoming air does not insure sterile conditions exist in the conduit or line connecting the filter to the chamber.

The present invention overcomes these and other problems and provides a combination fluid over-flow block/make-up air assembly that maintains sterile or microbially deactivated conditions between a make-up air filter and the chamber in a liquid sterilization or microbial deactivation system.

SUMMARY OF THE INVENTION

In accordance with a preferred embodiment of the present invention, there is provided a microbial deactivation system for sterilizing or microbially deactivating instruments and devices. The microbial deactivation system includes a circulation system for circulating a liquid microbial deactivation fluid through a chamber containing the instruments and devices. The chamber forms a portion of the circulation system. The microbial deactivation system further includes a fluid over-flow/make-up air assembly. The fluid over-flow/make-up air assembly includes a manifold having an inner cavity that is in fluid communication with the circulation system, an overflow port in the manifold, and an overflow valve assembly disposed in the manifold allowing fluid flow from the cavity to the overflow port when a pressure in the cavity exceeds a pressure in the overflow port by a predetermined amount. A filter assembly is attached to the manifold. The filter assembly has a filter valve assembly in communication with the cavity. The filter assembly is operable to allow air through the filter assembly into the cavity when the pressure within the cavity is a predetermined amount less than the pressure within the filter assembly.

In accordance with another aspect of the present invention, there is provided a filter assembly for use on a microbial deactivation or sterilization apparatus for providing filtered air thereto. The filter assembly has an air inlet, an air outlet and an air passage extending between the air inlet and the air outlet. A filter medium is disposed within the air passage between the air inlet and the air outlet. The filter medium is bacteria-retentive. A directional valve assembly is disposed within the passage between the filter medium and the air outlet for regulating the flow of air through the passage. The valve assembly permits air flow only in a direction from the air inlet to the air outlet. The air passage between the filter medium and the directional valve assembly is microbially deactivated.

In accordance with another aspect of the present invention, there is provided a filter assembly for use on a microbial deactivation or sterilization system for providing filtered air thereto. The assembly includes a filter canister containing a filter medium. The filter canister has an air inlet opening and an outlet opening. A mounting assembly is attached to the canister and has a fluid passage therethrough. The fluid passage has a first end and a second end. The first end of the fluid passage is in fluid connection with the outlet opening of the canister. A directional valve assembly is disposed within the fluid passage between the first end and the second end for regulating flow through the fluid passage. The valve assembly allows only flow in a direction from the first end to the second end of the fluid passage. The portion of the fluid passage between the valve assembly and the filter medium is microbially deactivated.

In accordance with yet another aspect of the present invention, there is provided a microbial deactivation or sterilization system for sterilizing or microbially deactivating instruments and devices. The system includes a circulation system for circulating a liquid microbial deactivation fluid through a chamber for containing the instruments and devices. The chamber forms a portion of the circulation system. The system also includes a fluid over-flow/make-up air assembly that includes a filter assembly for providing air to the circulation system. The filter assembly has an air inlet, an air outlet and an air passage extending between the air inlet and the air outlet. A filter medium is disposed within the air passage between the air inlet and the air outlet. The filter medium is bacteria-retentive. A directional valve assembly is disposed within the passage between the filter medium and the air outlet for regulating the flow of air through the passage. The valve assembly permits air flow only in a direction from the air inlet to the air outlet. The air passage between the filter medium and the directional valve assembly is microbially deactivated. The filter assembly is mounted to the microbial deactivation or sterilization system with the air outlet in fluid communication with the circulation system.

An advantage of the present invention is a combination fluid over-flow block/make-up air assembly for use in a reprocessor.

Another advantage of the present invention is a fluid over-flow block/make-up air assembly that maintains sterile conditions between the make-up air filter and a sterilization chamber of a reprocessor.

A still further advantage of the present invention is a replaceable filter assembly that is mountable to the fluid over-flow block in fluid communication with a microbial deactivation or sterilization chamber of a reprocessor.

A still further advantage of the present invention is a filter assembly as described above that maintains sterile conditions between a make-up air filter and a sterilization chamber of the reprocessor.

These and other objects will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF PREFERRED EMBODIMENT

Figure 1:
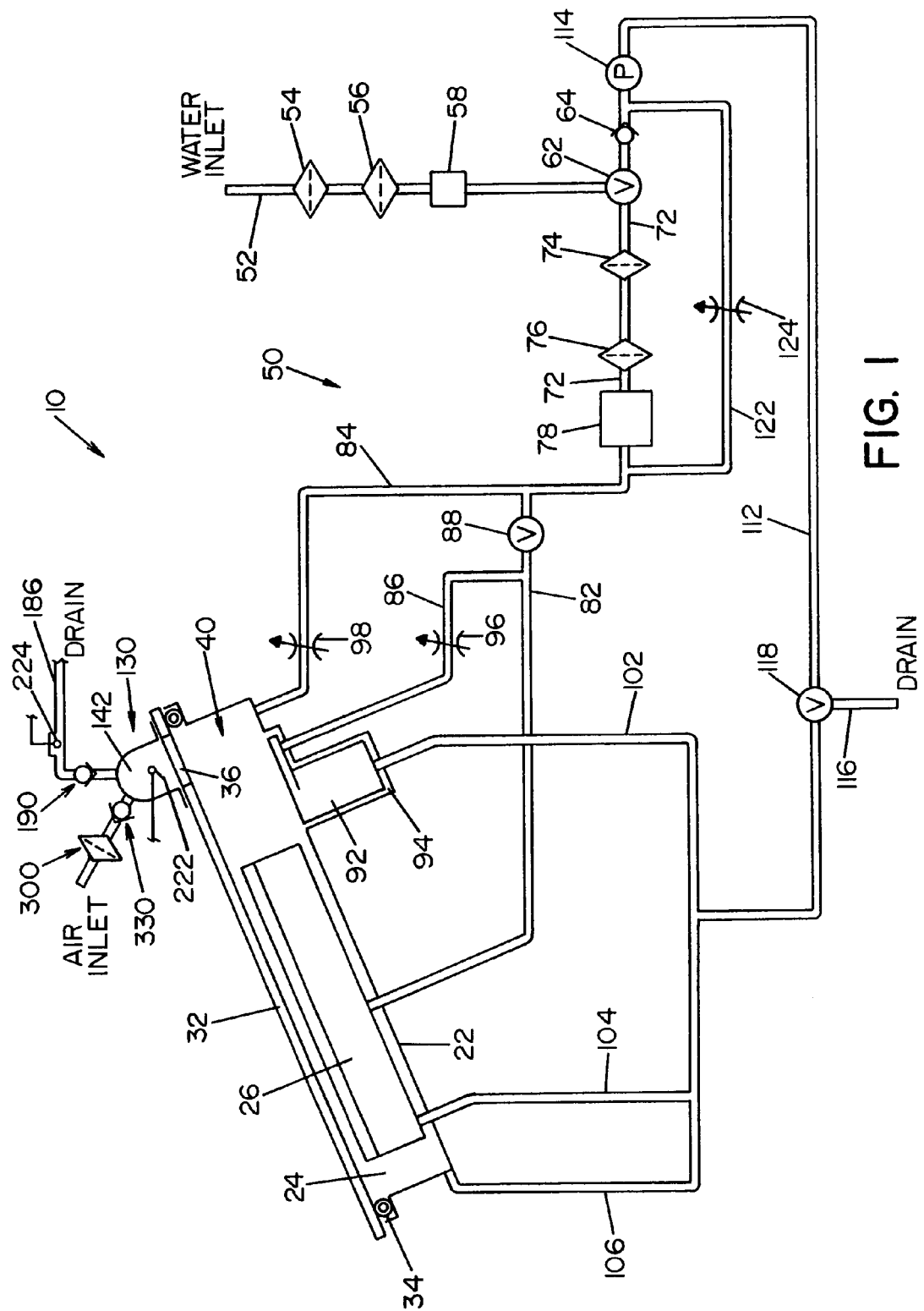
FIG. 1 is a schematic view of a microbial deactivation system with a fluid over-flow/make-up air assembly, according to a preferred embodiment of the present invention.

Referring now to the drawings wherein the showings are for the purpose of illustrating a preferred embodiment of the invention only, and not for the purpose of limiting same, FIG. 1 shows a simplified, schematic piping diagram of a microbial deactivation apparatus 10 having a fluid over-flow block/make-up air assembly, illustrating a preferred embodiment of the present invention.

Panel 22, that is part of a housing structure (not shown), defines a recess or cavity 24 dimensioned to receive items or instruments to be microbially deactivated. In the embodiment shown, a tray or container 26 is provided to receive the devices or instruments to be deactivated. Container 26 is dimensioned to be received within the recess or cavity 24, as illustrated in FIG. 1.

A manually operable lid 32 is movable between an opened position allowing access to cavity 24, and a closed position (shown in FIG. 1) closing or covering cavity 24. Seal element 34 surrounds cavity 24 and forms a fluid-tight seal between lid 32 and panel 22 when lid 32 is in a closed position. Latch means (not shown) are provided for latching and securing lid 32 in a closed position during a deactivation cycle. Cavity 24 essentially defines a chamber 40 when lid 32 is in a closed position.

A fluid circulation system 50 provides the microbial deactivation fluid to chamber 40 and is further operable to circulate the microbial deactivation fluid through chamber 40. Fluid circulation system 50 includes water inlet line 52 that is connected to a source of heated water (not shown). A pair of macro filters 54, 56 are provided in water inlet lines 52 to filter large contaminants that may exist in the incoming water. An ultraviolet (UV) treatment device 58 for killing organisms within the water source is preferably provided in the inlet lines. A water valve 62 controls the flow of water from water inlet line 52 to a system feeder line 72. System feeder line 72 includes two micro filters 74, 76 in series to filter microscopic organisms and particles from the incoming water so as to provide sterile water to fluid circulation system 50. A fluid heating device 78 is disposed in feeder line 72 downstream of micro filters 74, 76. System feeder line 72 splits into first branch feeder line 82 and secondary branch feeder line 84. First branch feeder line 82 communicates with container 26 within chamber 40. Secondary branch feeder line 84 is connected to chamber 40 itself. A secondary branch feeder line 86 splits off of first branch feeder line 82 and is directed to the inlet portion of chemical dispensing container 92 that contains dry chemical reagents that form the anti-microbial fluid used in microbial deactivation apparatus 10. A valve 88 controls flow through first branch feeder line 82 and through secondary branch feeder line 86 to chemical dispensing container 92. Chemical dispensing container 92 is disposed within a well 94 formed within panel 22 of the housing structure. A flow restrictor 96 is provided in secondary branch feeder line 86 to limit flow therethrough. A flow restrictor 98 is provided in second branch feeder line 84 to limit flow therethrough.

A branch return line 102 extends from chemical dispenser 92 and is connected to system return line 112. Likewise, branch fluid return lines 104, 106 extend from container 26 and chamber 40 respectively, and are connected to system return line 112. System return line 112 connects back with water inlet line 52 and fluid feeder line 72, as illustrated in FIG. 1. Pump 114 is disposed within system return line 112. Pump 114 is operable to circulate fluid through fluid circulation system 50. A drain line 116 is connected to system return line 112. A drain valve 118 controls fluid flow to the drain line 116.

A directional check valve 64 is disposed in system feeder line 72 between water inlet line 52 and pump 114. A filter bypass line 122 communicates with system feeder line 72 on opposite sides of filters 74, 76. Specifically, one end of bypass line 122 is connected to system feeder line 72 between pump 114 and directional check valve 64. The other end of bypass line 122 communicates with system feeder line 72 beyond filters 74, 76 and heating device 78, but before where first and second branch feeder lines 82, 84 are formed. A flow restrictor 124 is provided in filter bypass line 132 to limit flow therethrough.

A system microprocessor (not shown) controls the operation of circulation system 50, as shall be described in greater detail below. The operation of circulation system 50 includes a fill mode, a circulation mode and a drain mode, as shall also be described in greater detail below. To facilitate operation of the fill mode, circulation mode and drain mode, a fluid over-flow/make-up air assembly 130 is attached to lid 32 in fluid communication with chamber 40.

Figure 2:
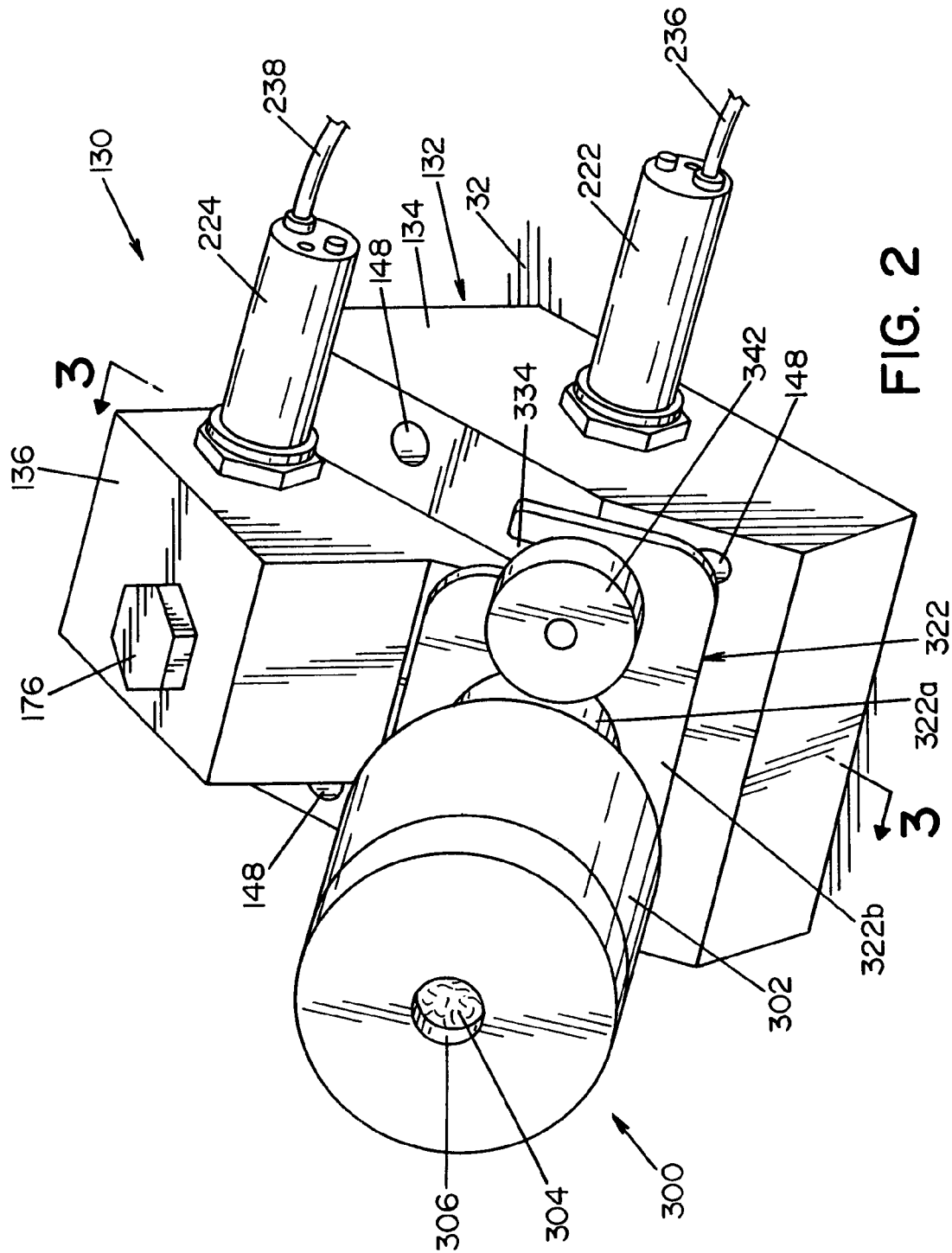
FIG. 2 is a perspective view of a fluid over-flow block with make-up assembly, illustrating a preferred embodiment of the present invention.
Figure 3:
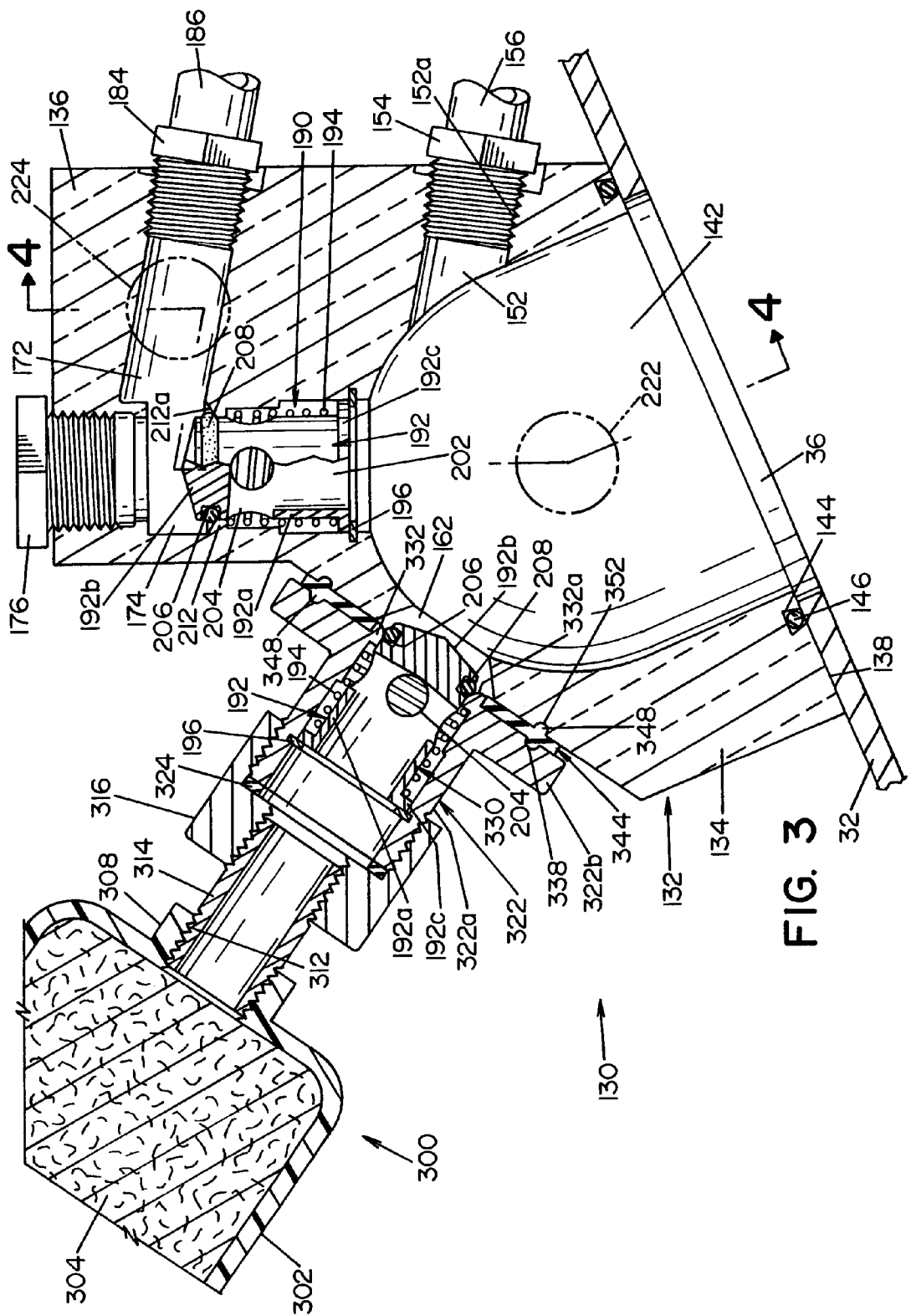
FIG. 3 is a sectional view taken along lines 3—3 of FIG. 2.

Referring now to FIGS. 2–6, fluid over-flow/air make-up assembly 130 is shown. Fluid over-flow/air make-up assembly 130 includes a manifold 132 having a base section 134 and an upper section 136 that extends from base section 134. Base section 134 includes a first surface 138 dimensioned to matingly engage lid 32 of the reprocessor for mounting thereto. A cavity 142 having a semi-hemispherical dome portion extends into base section 134 of manifold 132 from the first surface. Base section 134 is dimensioned to be mounted to lid 32 with cavity 142 positioned over an opening 36 in lid 32, as best seen in FIG. 3. A recess or groove 144 is formed in the first surface 138 of base section 134 around cavity 142 to receive seal element 146 to provide a fluid-tight seal between manifold 132 and lid 32 when manifold 132 is mounted thereto. Manifold 132 is preferably mounted to lid 32 by conventional fasteners (not shown) through mounting holes 148 in base section 134, as best seen in FIG. 2.

First opening 152 is formed through one wall of base section 134 to communicate with cavity 142 at a predetermined location therein. First opening 152 defines a circulation port, as shall be described in greater detail below. First opening 152 is basically a cylindrical bore having internal pipe threads 152a dimensioned to receive a conventional hose fitting 154 for connecting a hose or tube 156 to base section 134 of manifold 132.

Figure 8:
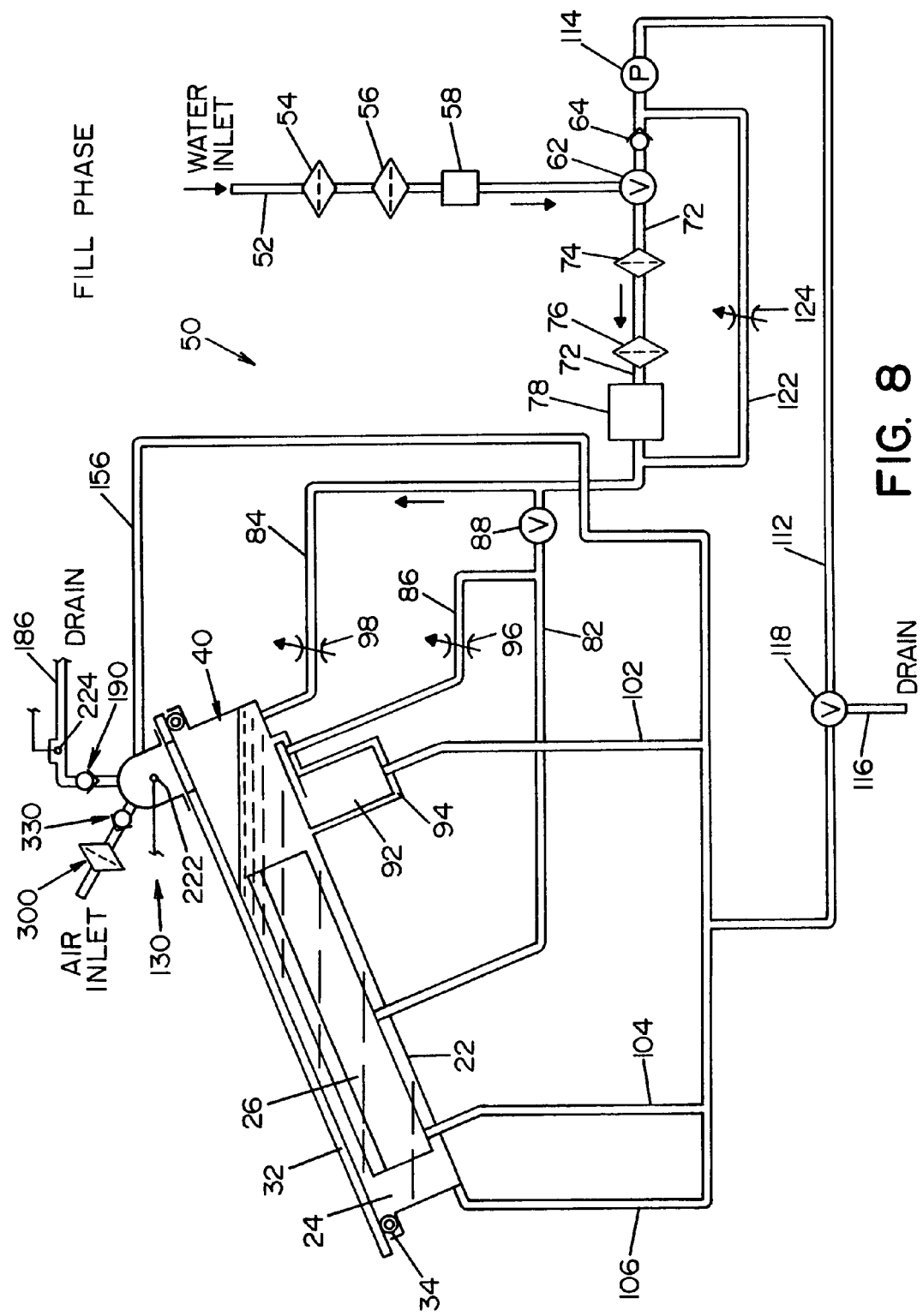
FIG. 8 is a schematic piping diagram of the microbial deactivation system schematically illustrating a fill cycle.
Figure 9:
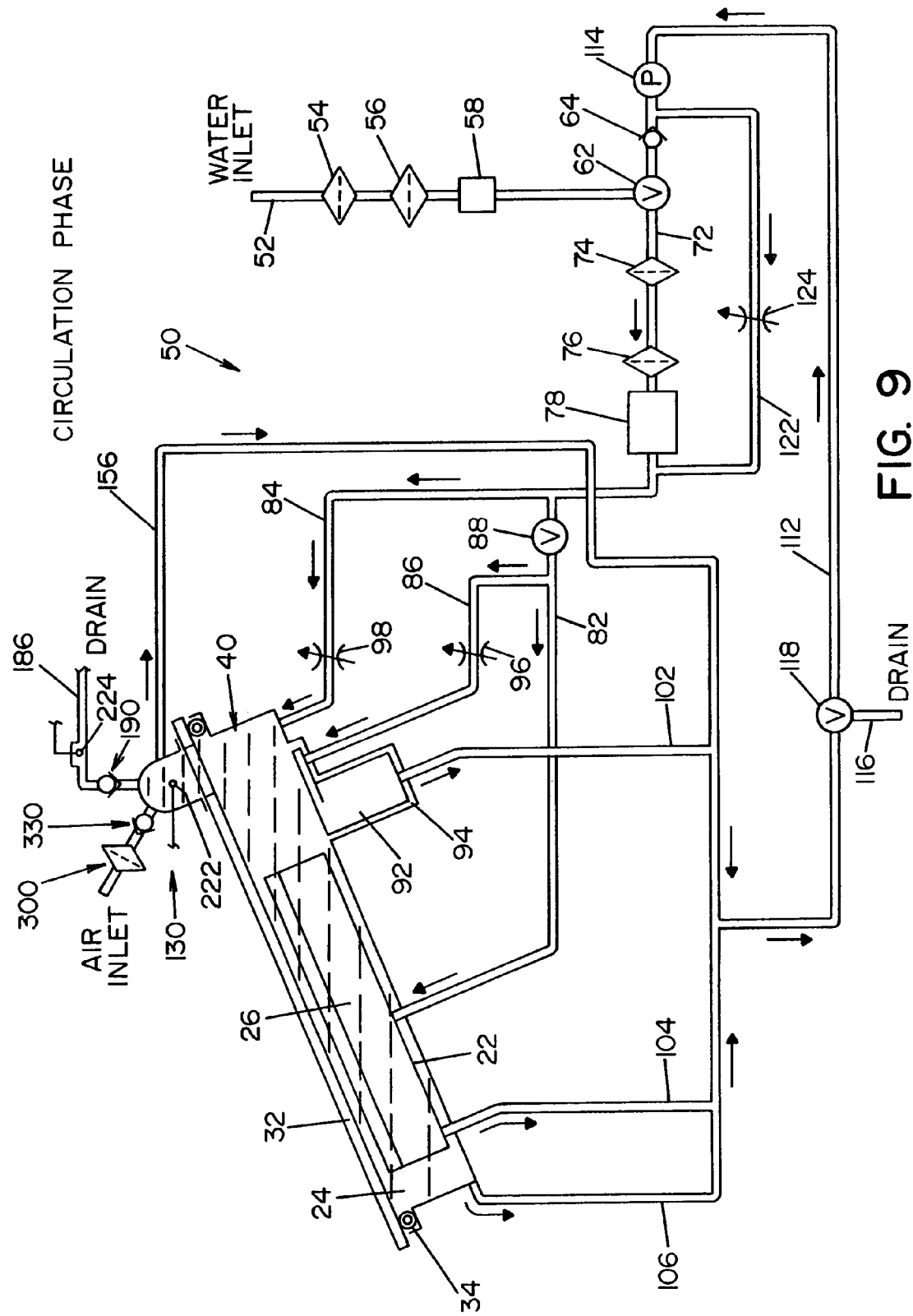
FIG. 9 is a schematic piping diagram of the microbial deactivation system illustrating a circulation cycle.
Figure 10:
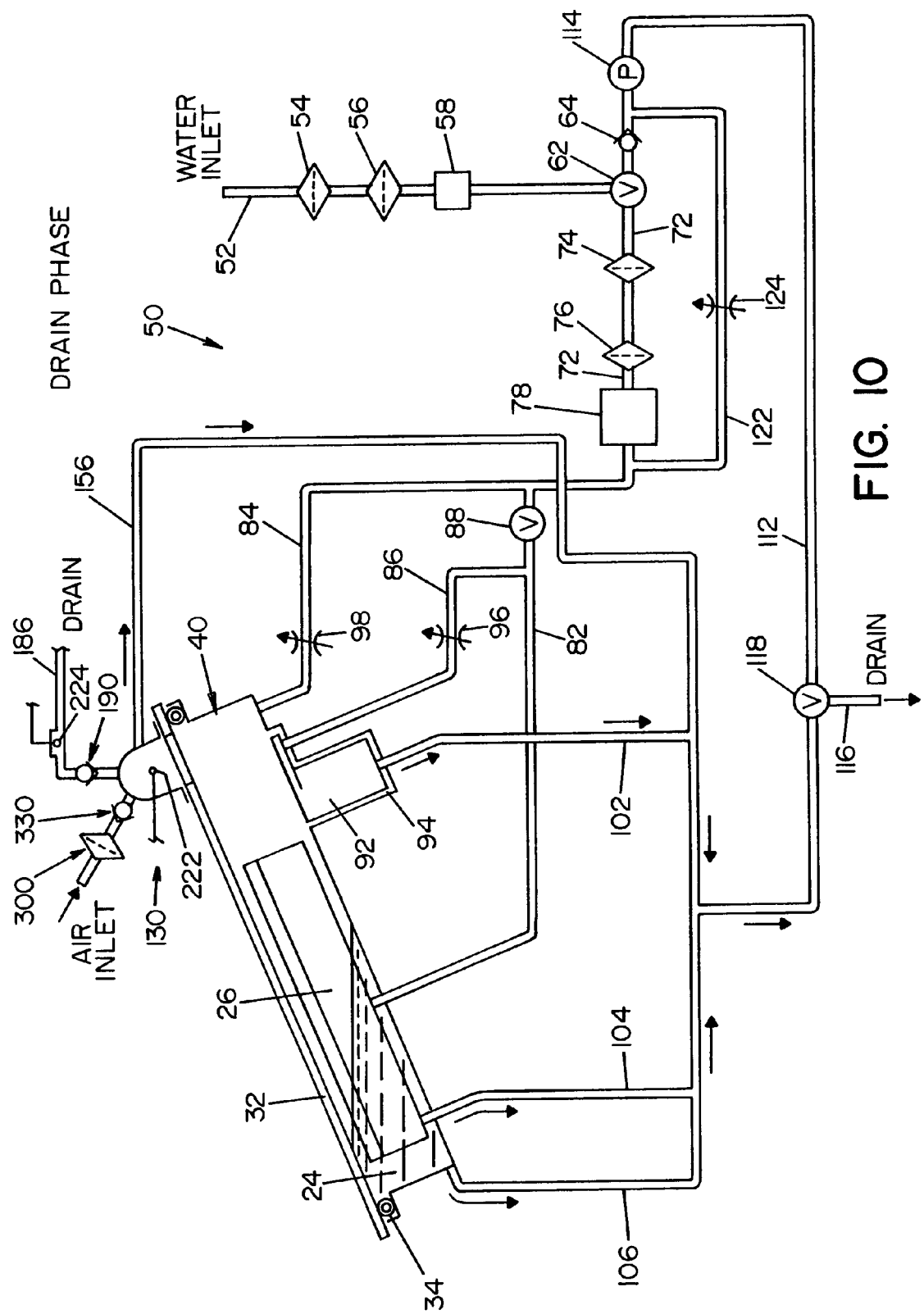
FIG. 10 is a schematic piping diagram of the microbial deactivation system illustrating a drain cycle.

In the embodiment shown, hose 156 defines fluid return lines 104, 106 that connect to system return line 112, as best seen in FIGS. 8, 9 and 10.

Second opening 162 is formed through the wall in base section 134 to communicate with the chamber. Second opening 162 defines an air make-up port. The air make-up port is provided to operatively engage a filter assembly 300, as shall be described in greater detail below.

Manifold 132 further includes a third opening 172 formed in upper section 136 of manifold 132. Third opening 172 defines an over-flow port. Third opening 172 communicates with manifold cavity 142 via a valve chamber 174. Valve chamber 174 extends from manifold cavity 142 through upper section 136. In the embodiment shown, valve chamber 174 is basically a cylindrical bore extending through upper section 136 of manifold 132 that extends into manifold cavity 142. The inner surface of valve chamber 174 where valve chamber 174 extends from upper section 136 of manifold 132 includes internal threads to matingly receive a conventional, threaded plug 176 that closes the upper end of valve chamber 174. The lower end of valve chamber 174 is formed to receive a directional check valve assembly 190, best seen in FIGS. 3 and 4. Third opening 172 communicates with valve chamber 174 above check valve assembly 190. Third opening 172 includes internal pipe threads dimensioned to receive a conventional hose fitting 184 for connecting a hose or tube 186 to third opening 172. Hose 186 is essentially a drain line 116, as schematically illustrated in FIG. 1.

Check valve assembly 190 includes a valve element 192, a biasing element 194 and a retaining ring 196. Valve element 192 has a generally cylindrical, tubular body 192a having a valve head 192b formed at one end thereof, and an outwardly extending flange 192c formed at the other end thereof. Valve head 192b defines a closed end of valve element 192, and the flange end defines an opened end of valve element 192. The body portion of valve element 192 defines an inner cavity 202. Openings 204 are formed in tubular body 192a to communicate with inner cavity 202. An annular groove 206 is formed in valve head 192b to receive an O-ring 208, as illustrated in FIGS. 3 and 4.

Valve element 192 is dimensioned to be disposed within valve chamber 174 in manifold 132. In this respect, valve chamber 174 includes an inwardly extending annular wall 212 having a champhered surface 212a that defines a valve seat for operative engagement with O-ring 208 and valve element 192. Retaining ring 196 is disposed within annular groove in the surface of valve chamber 174 and retains valve element 192 within valve chamber 174.

Biasing element 194 is a helical spring that surrounds tubular body 192a of valve element 192. Biasing element 194 is captured within valve chamber 174 between the flange 192c and annular wall 212 of valve chamber 174. Biasing element 194 is dimensioned to bias valve element 192 to a first closed position, wherein O-ring 208 on valve head 192b is seated against champhered surface 212a of annular wall 212. As shall be described in greater detail below, valve element 192 is movable between an open position, wherein openings 204 in valve element 192 are in fluid communication with third opening 172 when pressure within manifold cavity 142 exceeds pressure in third opening 172.

Figure 4:
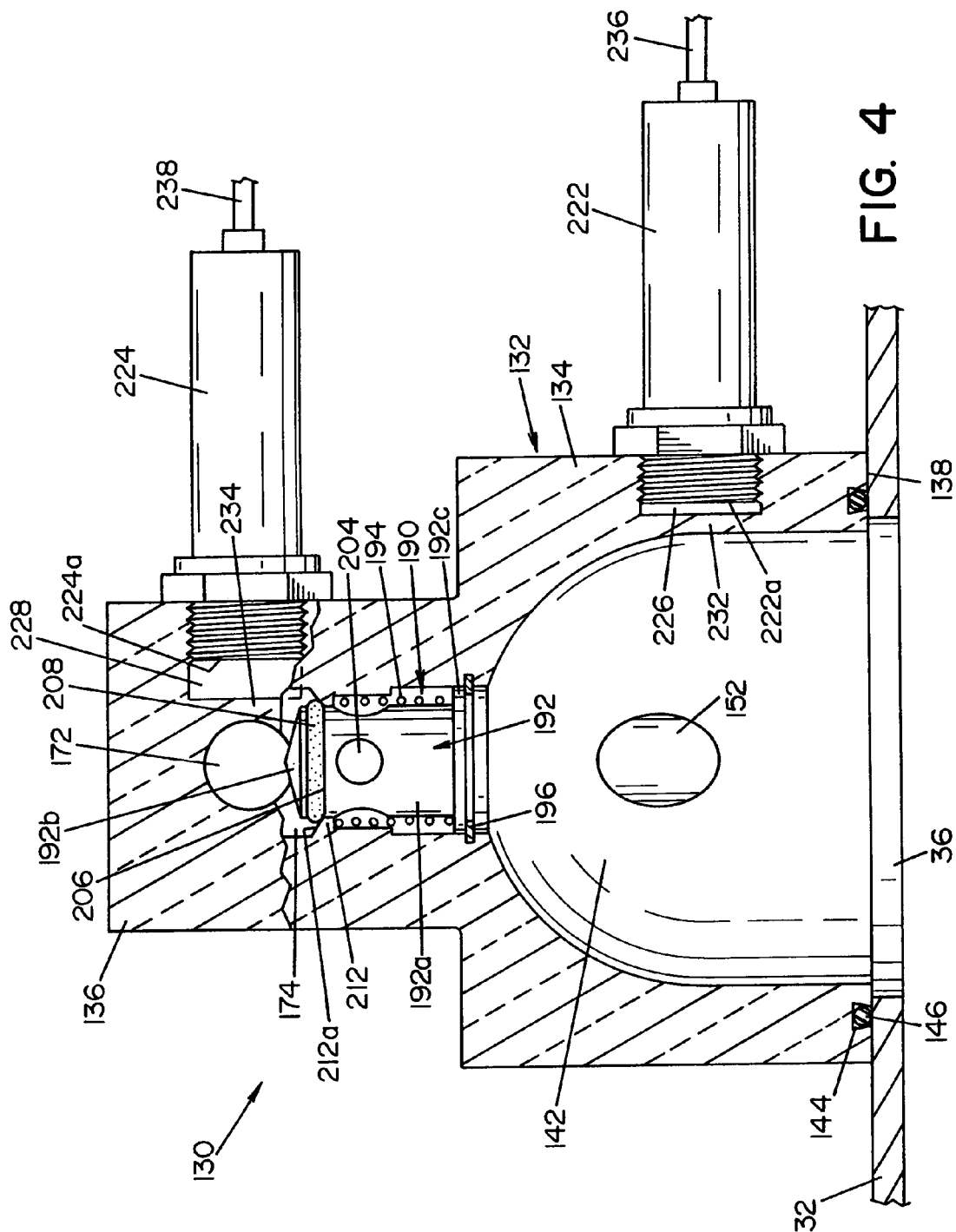
FIG. 4 is a sectional view taken along lines 4—4 of FIG. 3.

Two sensing elements 222, 224, best seen in FIGS. 2 and 4, are mounted to manifold 132. A first sensor element 222 is mounted to base section 134 in the vicinity of manifold cavity 142, and the second sensing element 224 is mounted to upper section 136 of manifold 132 in the vicinity of third opening 172, as best seen in FIG. 3. Sensing elements 222, 224 are operable to provide an indication when a microbial deactivation fluid is present in manifold cavity 142 and third opening 172, respectively. In the embodiment shown, sensing elements 222, 224 are capacitive sensors having threaded ends and sensor faces 222a, 224a. Sensor faces 222a, 224a are dimensioned to be received within threaded openings 226, 228 within base section 134 and upper section 136, respectively. As best seen in FIG. 4, threaded openings 226, 228 are dimensioned to form thin wall sections 232, 234 in base section 134 and upper section 136 of manifold 132. Sensing elements 222, 224 are preferably capacitive sensors. As will be appreciated from a further reading of the present specification, other types of sensor devices and arrangements may be used to sense the presence of the microbial deactivation fluid in manifold cavity 142 and third opening 172, and such other sensing devices are contemplated. In a preferred embodiment, sensing elements 222, 224 are capacitive sensors manufactured by Cutler-Hammer/Eaton Corporation, and sold under the trade designation Tubular Capacitive Proximity Sensor.

Electrical wires 236, 238 connect sensing elements 222, 224 to the system controller (not shown).

Figure 5:
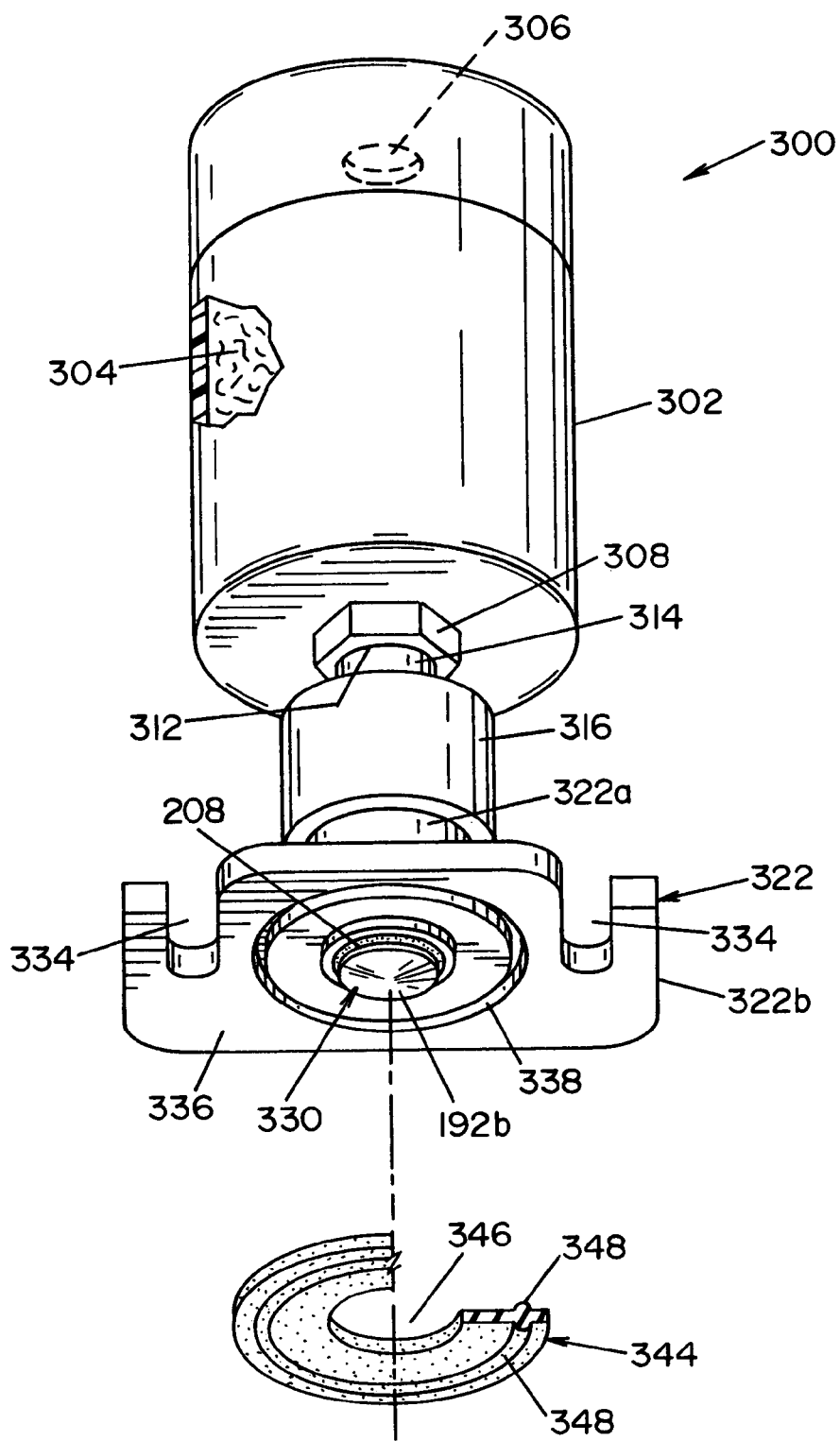
FIG. 5 is a partially broken, perspective view of an air make-up filter assembly and mounting gasket, illustrating another aspect of the present invention.

Referring now to FIG. 5, filter assembly 300 is best shown. In accordance with another aspect of the present invention, filter assembly 300 is a self-contained, replaceable unit that is releaseably mounted to manifold 132. Filter assembly 300 is comprised of a canister 302 containing a filter medium 304. Canister 302 is generally cylindrical in shape and has an opening 306 at one end and a collar 308 at the other end. Filter medium 304 is a bacteria-retentive material that has a minimum filtration efficiency of 99.97% for 0.3-micron particles. Filter medium 304 may be in the form of a capillary tube or hollow fiber membrane (or "fiber"), or in the form of a tubular sheath of a film, or a laminate sheet or film. Suitable filter medium material includes, by way of example and not limitation, PVDF, or PTFE (polytetraflouroethylene). A preferred filter medium is PTFE obtainable from Whatman Healthcare of Ann Arbor, Mich.

Collar 308 on canister 302 has an opening 312 therethrough that communicates with filter medium 304. Opening 312 in collar 308 is threaded to receive a tubular connector 314 that is threaded at both ends. The other end of connector 314 is attached to a coupling 316. Coupling 316 has internal threads adapted to attach canister 302 and connector 314 to a valve housing 322. Valve housing 322 has a tubular body portion 322a and a planar mounting portion 322b. A gasket 324 is disposed between coupling 316 and tubular body portion 322a of valve housing 322. A cylindrical cavity is defined through tubular body portion 322a and mounting plate 336. The cylindrical cavity is dimensioned to receive valve assembly 330 that in the embodiment shown is identical to valve assembly 190 as heretofore described. Since valve assembly 330 is identical to the valve assembly 190 previously described, like reference numbers are used to refer to like elements, and a detailed description of the respective elements of valve assembly 330 shall not be repeated. In this respect, valve assembly 330 within valve housing 322 includes a valve element 192, a biasing element 194 and a retaining ring 196.

Valve housing 322, coupling 316 and connector 314 essentially define a mounting assembly for mounting the filter canister to fluid over-flow/make-up assembly 130. In this respect, an air passage is formed in the mounting assembly through openings 204 in valve element 192, coupling 316 and connector 314.

Annular wall 332 is formed at the end of the valve cavity of valve housing 322. Annular wall 332 has a conical surface 332a that defines a valve seat to operatively engage, in sealing fashion, O-ring 208 on valve element 192. Referring now to FIG. 5, the mounting portion of valve housing 322 is best seen. Mounting portion 322b is preferably integrally formed with the tubular valve housing 322. Mounting portion 322b is essentially a flat, rectangular plate having a pair of spaced-apart slots 334 formed into one edge thereof. Slots 334 are formed on opposite sides of valve assembly 330. In the embodiment shown, mounting portion 322b has a planar mounting surface 336 having an annular groove 338 surrounding valve assembly 330.

Filter assembly 300 is dimensioned to be removeably mounted to manifold 132 with valve assembly 330 aligned, and in registry with, the air make-up port in base section 134 of manifold 132. In the embodiment shown, thumb screws 342, best seen in FIGS. 2 and 6, project through slots 334 in mounting portion 322b to secure filter assembly 300 to manifold 132. A gasket 344, best seen in FIG. 5, is disposed between mounting portion 322b and the base section of manifold 132 to form a fluid-tight seal therebetween. Gasket 344 is basically a flat, circular disk having a centrally located, circular opening 346 formed therethrough, and a concentric ridge 348 formed on each side thereof. The annular ridges are dimensioned to be received within annular groove 338 formed in mounting portion 322b and a corresponding groove 352 formed within the surface of base section 134 of manifold 132, as best seen in FIG. 3.

In accordance with another aspect of the present invention, the interior portion of filter assembly 300 is pre-sterilized or microbially deactivated. In this respect, a sterilant or microbial deactivation fluid may be drawn through filter assembly 300 by mounting filter assembly 300 to a fixture, wherein a low-pressure condition is created inside the fixture, i.e., around valve assembly 330, thereby causing valve assembly 330 to open and allowing a sterilant or a microbial deactivation fluid to be drawn through filter assembly 300. After the sterilization or deactivation process, removal of the low-pressure condition causes valve assembly 330 to return to its closed position, thereby sealing the interior of valve assembly 330, i.e., openings 204 defined by connector coupling 316 and valve body from the environment.

The present invention shall now further be described with reference to the operation of apparatus 10 and fluid over-flow/air make-up assembly 130. One or more items to be microbially deactivated or sterilized, such as medical, dental, pharmaceutical, veterinary or mortuary instruments or other devices are loaded into chamber 40. In the embodiment shown, the items would be loaded into container 26, which in turn would be placed into chamber 40. The items may be supported in a tray, basket, cartridge or the like (not shown) within chamber 40 or container 26.

The items are deactivated or sterilized with a microbial deactivation or sterilization fluid, such as a peracetic acid solution, which in a preferred embodiment is formed by exposing and mixing dry chemical reagents within the chemical dispensing device 92 with incoming water. In this respect, at the beginning of a deactivation operation, drain valve 118 in circulation system 50 is closed, and valve 62 in water inlet line 52 is opened to allow heated water to enter circulation system 50. Incoming water is first filtered by filters 54 and 56, and is then treated by a UV treatment device 58 that applies UV radiation to the water to reduce the level of viruses therein. The incoming water passes valve 62 and enters circulation system 50. The incoming water is then filtered by the filters in the feeder line, and proceeds to fill circulation system 50, chamber 40, and container 26.

The incoming water is under pressure from the external source, and forces air in circulation system 50, chamber 40, container 26 and to fluid over-flow/air make-up assembly 130. In this respect, since manifold 132 is disposed at the highest point of apparatus 10, air within the system migrates toward manifold cavity 142. Eventually, the trapped air within cavity 142 of manifold 132 will reach a pressure sufficient to force valve element 192 of valve assembly 190 to an opened position, allowing air within apparatus 10 to be vented from the system through third opening 172 to a drain. In this respect, valve assembly 190 is a directional check valve operable to release fluid (gas/liquid) from manifold cavity 142, but prevents flow from third opening 172 into the chamber.

Figure 6:
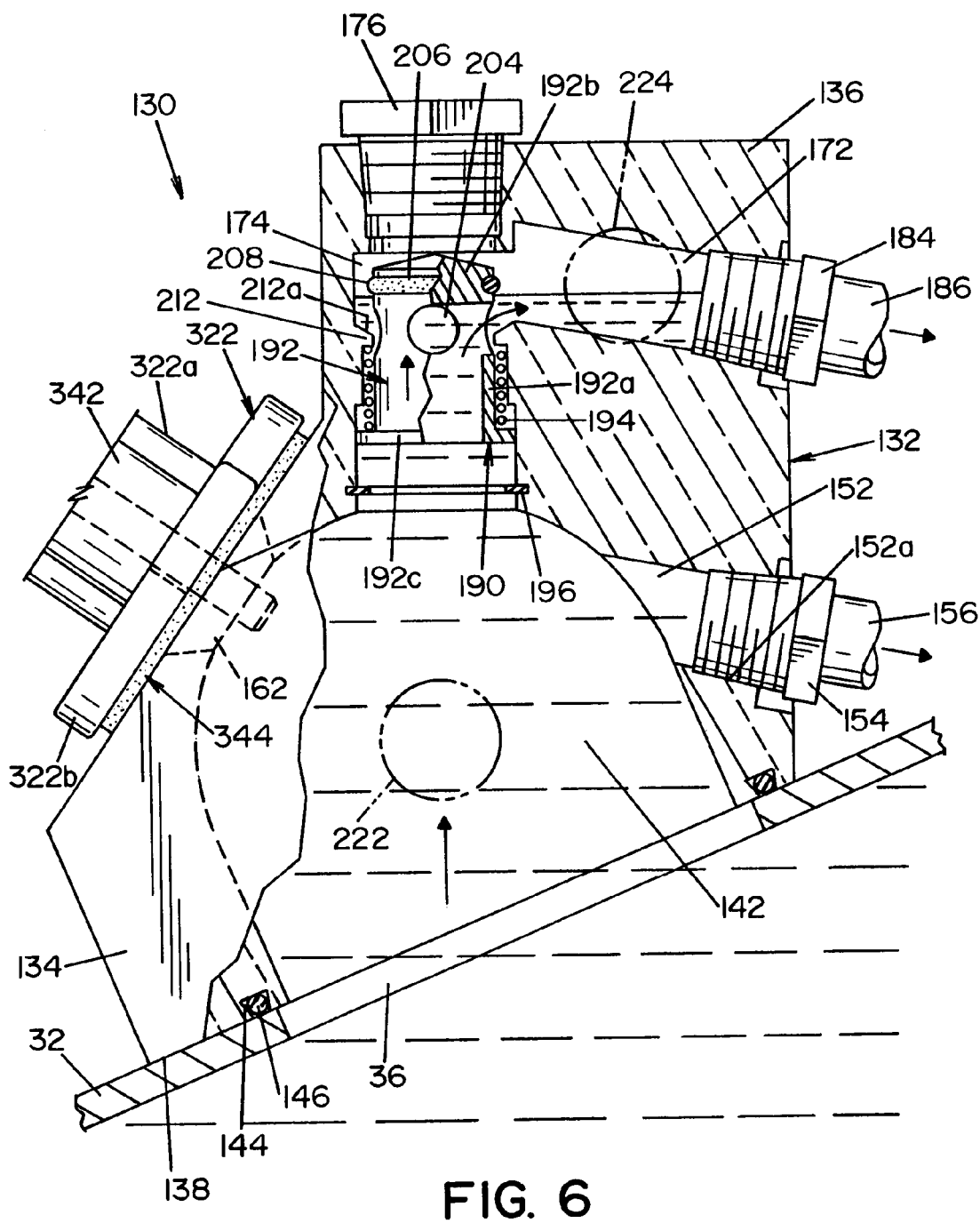
FIG. 6 is a cross-sectional view of the fluid over-flow/make-up air assembly, showing the fluid over-flow block during a fill cycle of the deactivation system.

The water level within chamber 40 will continue to rise until water fills cavity 142 of manifold 132 and forces valve element 192 of valve assembly 190 to move to an opened position, thus allowing excess water to be drained through third opening 172 to drain line 186, as schematically illustrated in FIG. 6. At this point, all air within circulation system 50, container 26 and chamber 40 is preferably purged from apparatus 10. When the water level in manifold 132 reaches the level shown in FIG. 6, the presence of the water flowing through third opening 172 is sensed by sensing element 224, indicating to the controller that apparatus 10 is filled. The system controller based upon a signal from sensing element 224 causes water valve 62 to close, thereby stopping the flow of water into apparatus 10, i.e., into circulation system 50, chamber 40 and container 26.

The foregoing description basically describes a fill phase of apparatus 10, and is schematically illustrated in FIG. 8.

During the fill phase, sensing element 224 will detect the presence of fluid within manifold cavity 142. Valve assembly 330 of filter assembly 300 prevents the flow of fluid from manifold cavity 142 into the interior of filter assembly 300.

Once apparatus 10 is filled, the system controller initiates a generation and exposure phase of operation, wherein pump 114 is energized to circulate water through circulation system 50, chamber 40 and container 26. Valve 88 in secondary branch line 86 is opened to create flow through chemical dispensing container 92. The water and dry chemical reagents within chemical dispensing container 92 form a microbial deactivation fluid that, as indicated above, in a preferred embodiment of the invention, is peracetic acid. The deactivation fluid formed from the dry chemical reagents flows into circulation system 50, wherein it is circulated through circulation system 50, chamber 40 and container 26 by pump 114, as is schematically illustrated in FIG. 9. In this respect, as indicated in the drawings, a portion of the deactivation fluid flows into chamber 40 around container 26 and a portion of the microbial deactivation fluid flows into and through container 26 and the items contained therein. As illustrated in FIG. 9, the microbial deactivation fluid circulates through manifold cavity 142 and through first opening 152, thereby exposing the surfaces within cavity 142 to the microbial deactivation fluid. During the generation and exposure phase of the deactivation cycle, sensing element 222 within base section 134 of manifold 132 monitors the level of the deactivation fluid within manifold cavity 142. If the fluid level should begin to drop, sensing element 222 will detect a lack of fluid in manifold cavity 142. Such a condition would cause the system to abort the cycle and sound an alarm. As discussed above, valve 62 is closed when sensing element 224 in third opening 172 senses fluid flowing therethrough.

Figure 7:
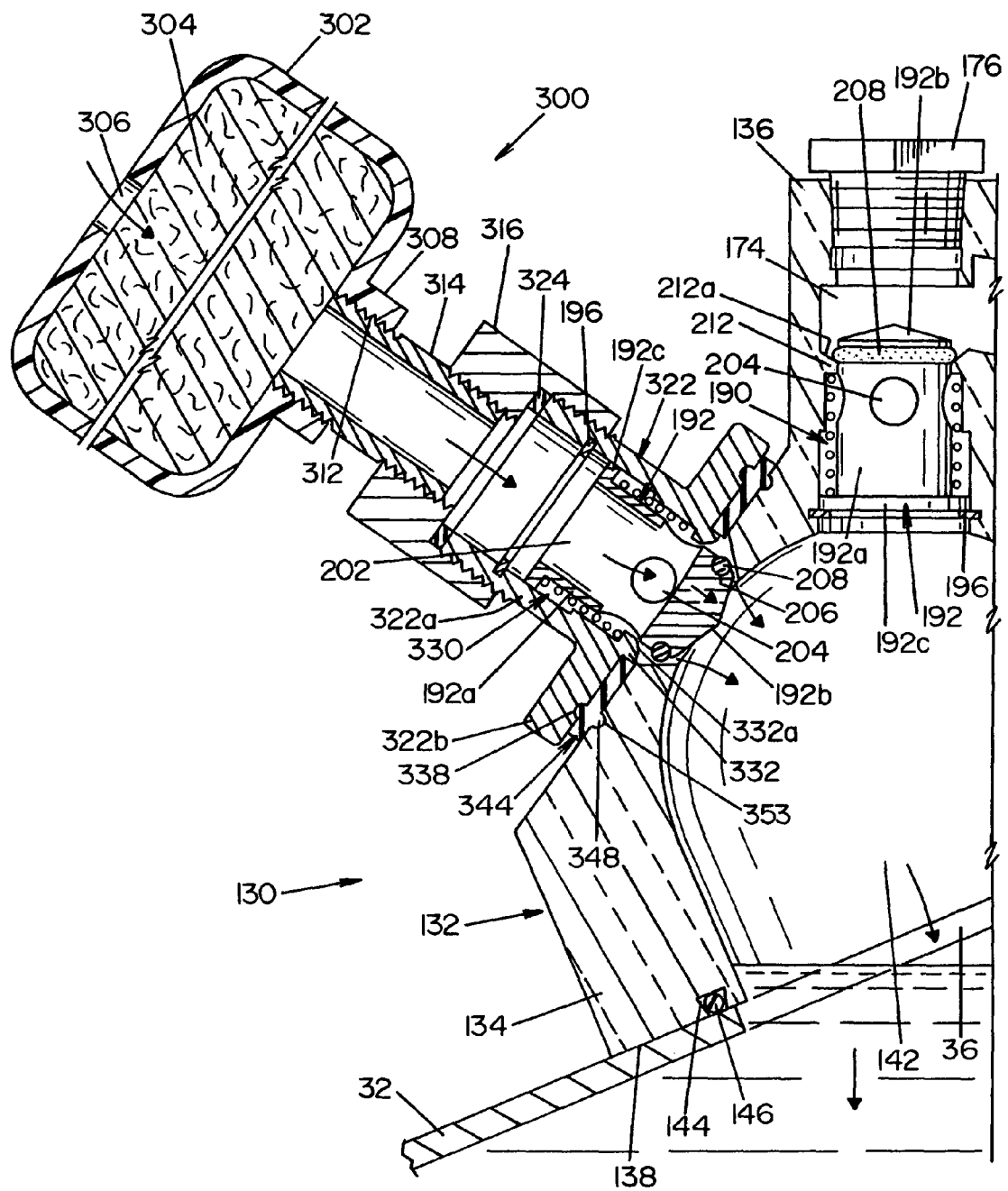
FIG. 7 is a cross-sectional view of the fluid over-flow/make-up air assembly during a drain cycle, wherein make-up air is being drawn into a sterilization or microbial deactivation chamber.

After a predetermined exposure period, a drain phase is initiated, as schematically illustrated in FIG. 10. Drain valve 118 is opened and the microbial deactivation fluid is drained from circulation system 50, chamber 40 and container 26. To allow efficient draining of apparatus 10, make-up air is drawn into manifold 132 through filter assembly 300, as illustrated by the arrows in FIG. 7. In this respect, valve assembly 330 within valve housing 322 moves to an opened position, when the pressure within manifold cavity 142 is less than the pressure within the passage defined by connector 314, coupling 316 and valve housing 322. This difference in air pressure results in airflow through filter canister 302 and filter medium 304, and through the air passage defined by connector 314, coupling 316 and valve housing 322. Air is drawn through opening 306 in filter canister 302 and through filter medium 304. The filtered air then flows through the passage defined by coupling 316, connector 314 and valve assembly 330 into manifold cavity 142. Since the interior of filter assembly 300, i.e., the interior of tubular connector 314, coupling 316 and valve assembly 330 is sterile or microbially deactivated, uncontaminated, filtered air is drawn into manifold cavity 142 and apparatus 10. Since valve head 192b and O-ring 208 that is attached thereto are sterile or microbially deactivated as a result of the exposure to the microbial deactivation or sterilization fluid during the deactivation or sterilization phase, the interior of valve assembly 330 is not exposed to a non-sterile or non-microbially deactivated environment.

Upon completion of the drain phase, drain valve 118 is closed. When the pressure within apparatus 10 equalizes, valve element 192 of valve assembly 330 and filter assembly 300 will return to a closed position with the interior of filter assembly 300 remaining sterile or microbially deactivated. Since the exposed portion of valve head 192b, i.e., the portion of valve head 192b facing manifold cavity 142, will always be exposed to the microbial deactivation fluid prior to the opening of valve assembly 330 during a drain phase, the interior of filter assembly 300 remains sterile or microbially deactivated.

After a predetermined number of uses, filter assembly 300 may be replaced with a new sterile or microbially deactivated filter assembly 300, and the initial sterilization or microbial deactivation phase of apparatus 10 will sterilize or microbially deactivate the outer facing surface of valve head 192b thereby again insuring sterile or microbially deactivated conditions when valve assembly 330 opens during a drain phase.

After the microbial deactivation fluid has been drained from apparatus 10, one or more rinsing phases are performed to rinse any residual microbial deactivation fluid and any residual matter from the deactivated items. In this respect, inlet valve 62 is opened to introduce fresh water into apparatus 10, in a manner as heretofore described as the fill phase. After each rinse fill, the rinse water is drained from apparatus 10 as heretofore described. Pump 114 may be activated to circulate the rinse water through apparatus 10. During each fill, circulation and drain phase, the fluid over-flow/air make-up assembly operates to maintain a sterile or microbially deactivated, internal environment within the system.

The present invention thus provides a fluid over-flow/air make-up assembly 130 for use in a reprocessor and includes a sterilized or microbially deactivated, replaceable filter assembly 300 for use therewith.

While the foregoing operation has been described with particular reference to peracetic acid sterilization systems, it would be appreciated that other microbial deactivants, such as hydrogen peroxide and solution, phenolic fluids, aldehyde-containing fluids and the like may alternatively be employed.

The foregoing description is a specific embodiment of the present invention. It should be appreciated that this embodiment is described for purposes of illustration only, and that numerous alterations and modifications may be practiced by those skilled in the art without departing from the spirit and scope of the invention. For example, in the embodiment shown, opening 152 defines a circulation port for circulating fluid through manifold 132. In some applications, opening 152 may not be required, and the flow of sterilant or microbially deactivated fluid through third opening 172 is sufficient to sterilize or microbially deactivate cavity 142 of manifold 132. It is intended that all such modifications and alterations be included insofar as they come within the scope of the invention as claimed or the equivalents thereof.

What is claimed is:

1. In a system for sterilizing or microbially deactivating instruments and devices, said system having a circulation system for circulating a microbial deactivation fluid through a chamber for containing said instruments and devices, said chamber forming a portion of said circulation system, a fluid over-flow and make-up air assembly, comprised of:

a manifold having an inner cavity that is in fluid communication with said circulation system;

an overflow port in said manifold;

an overflow valve assembly disposed in said manifold allowing fluid flow from said cavity to said overflow port when a pressure in said cavity exceeds a pressure in said overflow port by a predetermined amount; and a filter assembly attached to said manifold, said filter assembly having a filter valve assembly, an interior passage and a filter membrane, a portion of said filter valve assembly being exposed to said passage of said filter assembly and another portion of said filter valve assembly being exposed to said cavity, said filter assembly being sterile from said membrane to said filter valve assembly, said filter assembly operable to allow air through said filter assembly into said cavity when the pressure within said cavity is a predetermined amount less than the pressure within said filter assembly.

2. A system as defined in claim 1, wherein said filter assembly is releasably mounted to said manifold.

3. A system as defined in claim 1, further comprising an overflow sensing element mounted to said manifold, said first overflow sensing element operable to sense the flow of liquid through said overflow port.

4. A system as defined in claims 1 or 3, further comprising a circulation sensing element mounted to said manifold operable to sense when fluid is within said cavity.

5. A system as defined in claim 1, further comprising a circulation port in said manifold, said port communicating at one end to said cavity and at the other end to said circulation system to form a fluid path from said circulation system through said cavity and circulation port back to said circulation system, wherein said microbial deactivation fluid flows through said cavity during a deactivation cycle of said system.

6. A system as defined in claim 1, wherein said overflow valve assembly and said filter valve assembly are formed from the same valve components.

7. A system as defined in claim 1, wherein said manifold is in fluid communication with said chamber.

8. In a system for sterilizing or microbially deactivating instruments and devices, said system having a circulation system for circulating a microbial deactivation fluid through a chamber for containing said instruments and devices, said chamber forming a portion of said circulation system, a fluid over-flow and make-up air assembly, comprised of:
 a manifold having an inner cavity that is in fluid communication with said chamber, said cavity in said manifold including a semi-hemispherical portion;
 an overflow port in said manifold disposed above said semi-hemispherical portion;
 an overflow valve assembly disposed in said manifold above said semi-hemispherical portion allowing fluid flow from said cavity to said overflow port when a pressure in said cavity exceeds a pressure in said overflow port by a predetermined amount; and
 a filter assembly attached to said manifold, said filter assembly having a filter valve assembly in communication with said cavity, said filter assembly operable to allow air through said filter assembly into said cavity when the pressure within said cavity is a predetermined amount less than the pressure within said filter assembly.

9. A system as defined in claims 1, 2, or 7, wherein the system includes a source of peracetic acid which is the microbial deactivation fluid circulated through said system.

10. A replaceable, integral filter assembly for use on a sterilization or microbial deactivation apparatus for providing filtered air thereto, said filter assembly comprised of:
 an air inlet;
 an air outlet;
 an air passage extending between said air inlet and said air outlet;
 a filter medium disposed within said air passage between said air inlet and said air outlet; and
 a directional valve assembly disposed within said passage between said filter medium and said air outlet for regulating the flow of air through said passage, said directional valve assembly permitting air flow only in a direction from said air inlet to said air outlet, said air passage between said filter medium and said directional valve assembly being sterile or microbially deactivated; and
 a mounting portion for attaching said filter assembly in its entirety to said sterilization or microbial decontamination system, said mounting portion including a means to quickly secure or release said filter assembly from said sterilization or microbial decontamination system while maintaining said air passage sterile.

11. A filter assembly as defined in claim 10, wherein said filter medium is a bacteria-retentive filter.

12. A filter assembly as defined in claim 11, wherein said filter medium has a minimum filter efficiency of 99.97% for 0.3-micron particles.

13. A filter assembly as defined in claim 12, wherein said filter medium is polytetrafluoroethylene or poly(vinylidene fluoride).

14. A replaceable, integral filter assembly for use on a sterilization or microbial deactivation system for providing filtered air thereto, said assembly comprised of:
 a filter canister containing a filter medium, said filter canister having an air inlet opening and an outlet opening;
 a mounting assembly attached to said canister having a fluid passage therethrough, said fluid passage having a first end and a second end, said first end of said fluid passage being in fluid connection with said outlet opening of said canister, said mounting assembly for attaching said filter assembly in its entirety to said sterilization or microbial deactivation system; and
 a directional valve assembly disposed within said fluid passage between said first end and said second end for regulating flow through said fluid passage, said valve assembly allowing only flow in a direction from said first end to said second end of said fluid passage, the portion of said fluid passage between said valve assembly and said filter medium being sterilized or microbially deactivated, said mounting assembly including a means to quickly secure and release said filter assembly from said sterilization or microbial deactivation system while maintaining said fluid passage sterile.

15. A filter assembly as defined in claim 14, wherein said filter medium is a bacteria-retentive filter.

16. A filter assembly as defined in claim 15, wherein said filter medium has a minimum filter efficiency of 99.97% for 0.3-micron particles.

17. A filter assembly as defined in claim 16, wherein said filter medium is polytetrafluoroethylene or poly(vinylidene fluoride).

18. In a system for sterilizing or microbially deactivating instruments and devices, said system having a circulation system for circulating a microbial deactivation fluid through a chamber for containing said instruments and devices, said chamber forming a portion of said circulation system, a fluid over-flow and make-up air assembly, comprised of:
 a filter assembly for providing air to said circulation system, said filter assembly having an air inlet, an air outlet and an air passage extending between said air inlet and said air outlet, a filter medium disposed within said air passage between said air inlet and said air outlet, a directional valve assembly disposed within said passage between said filter medium and said air outlet for regulating the flow of air through said passage, a mounting portion for attaching said filter assembly to said fluid over-flow and make-up air assembly, said valve assembly permitting air flow only in a direction from said air inlet to said air outlet, said air passage between said filter medium and said directional valve assembly being sterile or microbially deactivated, said mounting portion including a means to Quickly secure or release said filter assembly from said fluid over-flow and make-up air assembly while maintaining said air passage sterile.

19. A system as defined in claim 18, wherein said filter medium is a bacteria-retentive filter.

20. A system as defined in claim 19, wherein said filter medium has a minimum filter efficiency of 99.97% for 0.3-micron particles.

21. A system as defined in claim 20, wherein said filter medium is polytetrafluoroethylene or poly(vinylidene fluoride).

* * * * *